(12) United States Patent
Colucci et al.

(10) Patent No.: US 8,168,815 B2
(45) Date of Patent: May 1, 2012

(54) FUSED AROMATIC PTP-1B INHIBITORS

(75) Inventors: John Colucci, Kirkland (CA);
Marie-Claire Wilson, Russell (CA);
Yongxin Han, Kirkland (CA); Claude Dufresne, Dollard des Ormeaux (CA);
Michel Belley, Pierrefonds (CA); Cheuk K. Lau, L'lle-Bizard (CA); Christopher Bayly, Beaconsfield (CA)

(73) Assignee: Kaneq Pharma Inc., Boucherville, Quebec (CA)

( * ) Notice: Subject to any disclaimer, the term of this patent is extended or adjusted under 35 U.S.C. 154(b) by 447 days.

(21) Appl. No.: 12/518,899

(22) PCT Filed: Jan. 24, 2008

(86) PCT No.: PCT/CA2008/000172
§ 371 (c)(1),
(2), (4) Date: Jun. 12, 2009

(87) PCT Pub. No.: WO2008/089581
PCT Pub. Date: Jul. 31, 2008

(65) Prior Publication Data
US 2010/0022477 A1    Jan. 28, 2010

Related U.S. Application Data

(60) Provisional application No. 60/897,700, filed on Jan. 26, 2007.

(51) Int. Cl.
*C07D 215/38* (2006.01)
(52) U.S. Cl. ...................................................... 558/204
(58) Field of Classification Search .................. 546/153, 546/167, 23; 514/312; 558/204
See application file for complete search history.

(56) References Cited

FOREIGN PATENT DOCUMENTS

| WO | WO01/70754 A1 | 9/2001 |
|----|----|----|
| WO | WO2006/055525 A2 | 5/2006 |
| WO | WO2006/055525 A3 | 5/2006 |

OTHER PUBLICATIONS

Wang, J Biological Chem, vol. 283, No. 29, pp. 20277-20287, Jul. 20089.*
Montalibet, Biochem Pharm, vol. 68, pp. 1807-1814, 2004.*
Montalibet, J Biological Chem, vol. 281, No. 8, pp. 5258-5266, 2006.*
Dermer, Blo/Technology, vol. 12, pp. 320, 1994.*
Freshney (Culture of Animal Cells, A Manual of Basic Technique, Alan R Liss, Inc. 1983, New York, p. 4.*
Montalibet, J. et al., "Residues Distant from the Active Site Influence Protein-tyrosine Phosphatase 1B Inhibitor Binding", Journal of Biological Chemistry, 2006, pp. 5258-5266, vol. 281, No. 8.
Montalibet, J. et al., "Using yeast to screen for inhibitors of protein tyrosine phosphatase 1B", Biochemical Pharmacology, 2004, pp. 1807-1814, vol. 68.

* cited by examiner

*Primary Examiner* — D M Seaman
(74) *Attorney, Agent, or Firm* — Philippe D. Durette

(57) ABSTRACT

The invention encompasses the novel class of compounds represented by the formula below, which are inhibitors of the PTP-1B enzyme. The invention also encompasses pharmaceutical compositions which include the compounds shown (Formula I) above and methods of treating or preventing PTP-1B mediated diseases, including diabetes.

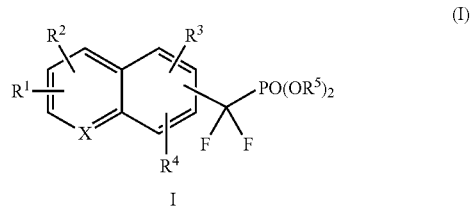

8 Claims, No Drawings

FUSED AROMATIC PTP-1B INHIBITORS

CROSS-REFERENCE TO RELATED APPLICATIONS

This application is a U.S. National Phase application under 35 U.S.C. §371 of PCT Application No. PCT/CA2008/000172, filed Jan. 24, 2008, which claims priority from and the benefit of U.S. Provisional Application No. 60/897,700, filed Jan. 26, 2007.

FIELD OF THE INVENTION

This invention relates to a novel class of phosphonic acid derivatives that are inhibitors of PTP-1B and that may be advantageous in the treatment of Type 2 diabetes and other PTP-1B mediated diseases.

BACKGROUND OF THE INVENTION

Protein tyrosine phosphatases are a large family of transmembrane or intracellular enzymes that dephosphorylate substrates involved in a variety of regulatory processes (Fischer et al., 1991, Science 253:401-406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252-5256; Goldstein, 1993, Receptor 3:1-15).

Numerous proteins are substrates of PTP-1B. One important substrate is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269: 1-4). This causes activation of the insulin receptor tyrosine kinase, which phosphorylates the various insulin receptor substrate (IRS) proteins that propagate the insulin signaling event further downstream to mediate insulin's various biological effects.

Kennedy et al., 1999, Science 283: 1544-1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Further support for the use of PTP-1B inhibitors to treat type 2 diabetes and related diseases has been provided by the use of antisense oligonuceotides specific for PTP-1B in animal models of type 2 diabetes. Inhibition of PTP-1B with anti-sense oligonucleotides in the animal models resulted in normalization of blood glucose and insulin levels. Zinker et al., 2002, Proc. Natl. Acad. Sci. USA, 99: 11357.

Compounds that inhibit PTP-1B are therefore expected to have utility for treating and/or controlling Type 2 diabetes and for improving glucose tolerance in patients in need thereof. Inhibitors of PTP-1B are also expected to be useful for delaying the onset of diabetes in pre-diabetic patients and for preventing pre-diabetic patients from developing diabetes. PTP-1B inhibitors should also have utility in treating obesity and dyslipidemia. Human drugs for treating diabetes by inhibiting PTP-1B have so far not been successfully developed. New chemical compounds that inhibit PTP-1B are needed.

Overexpression and elevated levels of PTP-1B have been observed in several cancer lines, including chronic myelogenous leukemia (CML), breast cancer, ovarian cancer, and prostate cancer, suggesting a regulatory role for PTP-1B in controlling kinase activity in these and other cancer cells. See for example, Liu, et al., J Biol. Chem., 1996, 271:31290-31295; Kenneth et al., Mol Cell Biol, 1998, 18:2965-2975; Weiner et al., J Natl. Cancer Inst., 1996, 86: 372-378. Thus inhibition of PTP-1B activity may constitute an important target for treating or preventing these and other cancers. PTP-1B inhibitors may thus be useful for treating or preventing cancer and for slowing the progression of cancer once it has developed.

Studies also suggest that PTP-1B inhibitors may be useful for treating or preventing neurodegenerative diseases.

SUMMARY OF THE INVENTION

Compounds represented by formula I, including pharmaceutically acceptable salts thereof, and prodrugs thereof, are PTP-1B inhibitors that may be useful in the treatment of diabetes and related medical conditions, and may also be useful in the treatment of other PTP-1B mediated diseases or conditions.

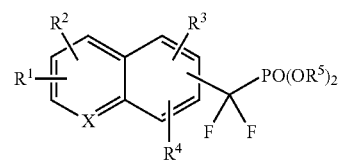

In the compounds of formula I:

X is selected from CH and N;

$R^1$ is selected from the group consisting of (a) $C_{1-3}$alkyl optionally substituted with 1-3 halogens and optionally with one group selected from —OH, —O$C_{1-3}$alkyl optionally substituted with 1-3 halogens, —SO$_x$$C_{1-3}$alkyl, and —CN, (b) —C(=O)H, (c) —C(=O)$C_{1-3}$alkyl optionally substituted with 1-3 halogens, (d) —CN, (e) —HC=NOH, (f) —(CH$_3$)C=NOH, (g) —HC=NO$C_{1-3}$alkyl optionally substituted with 1-3 halogens, (h) —(CH$_3$)C=NO$C_{1-3}$alkyl optionally substituted with 1-3 halogens (i) —C(=O)O$C_{1-3}$alkyl optionally substituted with 1-3 halogens, (j) —C(=O)NHR$^6$, (k) —CH=CH-Phenyl wherein —CH=CH— is optionally substituted with 1-2 substituents independently selected from halogen and $C_{1-2}$alkyl optionally substituted with 1-3 F, (l) —CH$_2$CH$_2$-Phenyl wherein —CH$_2$CH$_2$— is optionally substituted with 1-4 substituents independently selected from halogen and $C_{1-2}$alkyl optionally substituted with 1-3 F, (m) Phenyl, (n) -HET-Phenyl, wherein HET is a 5- or 6-membered heteroaromatic ring containing 1-3 heteroatoms selected from O, N and S, (o) —C≡C-Phenyl, and (p) —CH$_2$-Phenyl, wherein the —CH$_2$— group of —CH$_2$-Phenyl is optionally substituted with 1-2 substituents independently selected from halogen and $C_{1-2}$alkyl optionally substituted with 1-3 F, wherein Phenyl and HET in all occurrences are optionally substituted with 1-3 substituents independently selected from (i) halogen, (ii) —C(=O)O$C_{1-3}$alkyl optionally substituted with 1-3 halogens, (iii) —C(=O)OH (iv) $C_{1-3}$alkyl optionally substituted with 1-3 halogens, (v) —O$C_{1-3}$alkyl optionally substituted with 1-3 halogens, (vi) —SO$_x$Me, and (vii) —SO$_2$NH$_2$;

$R^6$ is selected from the group consisting of H, $C_{1-3}$alkyl optionally substituted with 1-3 halogens, Phenyl, and —CH$_2$-Phenyl, wherein Phenyl in both occurrences is optionally substituted with 1-3 substituents independently selected from (i) halogen, (ii) —C(=O)O$C_{1-3}$alkyl optionally substituted with 1-3 halogens, (iii) —C(=O)OH (iv) $C_{1-3}$alkyl optionally substituted with 1-3 halogens, and (v) —OC$_{1-3}$alkyl optionally substituted with 1-3 halogens;

R$^2$ and R$^4$ are independently selected from H, halogen, —CH$_3$, —CF$_3$, —OCH$_3$, and —OCF$_3$;

R$^3$ is halogen, wherein said halogen is bonded to the fused aromatic ring of Figure I at a position ortho to the —CF$_2$PO(OR$^5$)$_2$ group, Each R$^5$ group is independently selected from the group consisting of H and C$_{1-3}$alkyl optionally substituted with 1-3 halogens, and x is 0, 1, or 2.

Methods of treating and controlling diabetes, obesity, and other diseases and conditions using the compounds of Formula I are disclosed herein. Pharmaceutical compositions and combination treatments are also disclosed herein.

The compounds disclosed herein are a new class of PTP-1B inhibitors. The structure and name of one of the compounds (Example 7B) was disclosed in two publications, listed below, as a PTP-1B inhibitor. The synthesis of the compound was not disclosed in these publications: (1) Montalibet et al., *Biochemical Pharmacology*, 2004, 68:1807-1814, (2) Montalibet et al., *Journal of Biological Chemistry*, 2006, 281, No. 8: 5258-5266.

DETAILED DESCRIPTION OF THE INVENTION

The compounds of Formula I have numerous embodiments, as summarized below:

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also have utility in treating PTP1B mediated diseases. Inactive or less active diastereoisomers and enantiomers are useful for scientific studies relating to the receptor and the mechanism of activation.

The invention also includes pharmaceutically acceptable salts of the compounds, and pharmaceutical compositions comprising the compounds and a pharmaceutically acceptable carrier. The compounds are especially useful in treating insulin resistance, type 2 diabetes, and dyslipidemia that is associated with type 2 diabetes and insulin resistance. The compounds are also useful for treating obesity. They also are useful for treating certain kinds of cancer and for slowing the progression of cancer once it has developed in a patient. They are also useful for treating, preventing or slowing the progression of neurodegenerative disease.

The compounds disclosed herein may be used in pharmaceutical compositions comprising (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound of Formula I or a pharmaceutically acceptable salt thereof is the only active ingredient.

A compound of Formula I, or a pharmaceutically acceptable salt thereof, may be used in the manufacture of a medicament for the treatment of type 2 diabetes mellitus in a human or other mammalian patient.

A method of treating type 2 diabetes comprises the administration of a therapeutically effective amount of a compound of Formula I, or a pharmaceutically acceptable salt thereof, or a pharmaceutical composition comprising the compound, to a patient in need of treatment. Other medical uses of the compounds of Formula I are described hereinafter.

Abbreviations

Abbreviations and terms that are commonly used in the fields of organic chemistry, medicinal chemistry, pharmacology, and medicine and are well known to practitioners in these fields are used herein. Representative abbreviations and definitions are provided below:

Ac is acetyl [CH$_3$C(O)—]; Ac$_2$O is acetic anhydride; 9-BBN is 9-borabicyclo[3.3.1]nonane; Bn is benzyl; BOC is tert Butyloxycarbonyl; DIAD is diisopropylazodicarboxylate; DIBAL is diisobutylaluminum hydride; DMF is N,N-dimethylformamide; DMSO is dimethyl sulfoxide; EDAC (or EDC) is 1-ethyl-3-[3-(dimethylamino)propyl]-carbodiimide HCl; Et$_3$N is triethylamine; Et is ethyl; EtOAc is ethyl acetate; EtOH is ethanol; 3-F-Ph is 3-fluorophenyl, HCl is hydrochloric acid; HOBt is 1-hydroxybenzotriazole; HPLC is high performance liquid chromatography; LCMS is HPLC with mass Spectral detection; LG is leaving group; M is molar; mmol is millimole; Me is methyl; MeOH is methanol; MsCl methanesulfonyl chloride; N is normal; NaHMDS is sodium hexamethyldisiliazide; NaOAc is sodium acetate; NaOtBu is sodium tert-butoxide; NMO is N-methylmorpholine N oxide; NMP is N Methyl pyrrolidinone; Pd(dba)$_2$ is tris(dibenzylideneacetone)dipalladium; PdCl$_2$(Ph$_3$P)$_2$ is dichlorobis-(triphenylphosphene)palladium; PG Denotes an unspecified protecting group; Ph is phenyl; PhMe is toluene; PPh$_3$ is triphenylphosphine; PMB is para-methoxybenzyl; RT is room temperature; TBAF is tetrabutyl ammonium fluoride; TBS is tert-butyldimethylsilyl; tBu is tert-butyl; Tf is triflate; TFA is trifluoroacetic acid; THF is tetrahydrofuran; TLC is thin layer chromatography; TMS is trimethylsilyl; TPAP is tetrapropylammonium perruthenate.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. Cycloalkenyl rings comprise a double bond in the ring.

"Aryl" is commonly used to refer to carbocyclic aromatic structures. The most common aryl groups are phenyl and naphthyl. Phenyl is generally the most preferred aryl group.

"Heterocycle" means a saturated or partially unsaturated ring or ring system containing at least one heteroatom selected from N, S and O, wherein the number of heteroatoms and the ring size and the degree of unsaturation (if any) are defined herein. Examples of heterocycles include tetrahydrofuran, piperazine, piperidine, and morpholine.

"Heteroaryl" means a heteroaromatic ring containing at least one ring heteroatom selected from N, O and S (including SO and $SO_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like.

"Halogen" includes fluorine, chlorine, bromine and iodine.

"Me" represents methyl.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, individual diastereomers, and mixtures of diastereomers and/or enantiomers. The invention is meant to comprehend all such isomeric forms of the compounds of Formula I. Specifically, the compounds of the instant invention have at least three asymmetric centers. Additional asymmetric centers may be present depending upon the nature of the various substituents on the molecule. It is intended that all of the possible optical isomers, stereoisomers, and diastereomers in mixtures and as pure or partially purified compounds are included within the scope of this invention (i.e. all possible combinations of the asymmetric centers as pure compounds or in mixtures).

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, or when it has a basic substituent group in its structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

The invention includes therapeutically active metabolites, where the metabolites themselves fall within the scope of the claims. The invention also includes prodrugs, which are compounds that are converted to the claimed compounds as they are being administered to a patient or after they have been administered to a patient. The claimed chemical structures of this application in some cases may themselves be prodrugs.

Utilities

The compounds specifically exemplified herein exhibit good efficacy in inhibiting the PTP-1B enzyme, as shown by their in vitro assays. The compounds generally have an $IC_{50}$ value of less than 2 µM in the enzyme assay described in the Assays section, and preferably have an $IC_{50}$ value of less than 1 µM.

Inhibitors of PTP-1B improve insulin-sensitivity and may have utility in preventing or treating diabetes, improving glucose tolerance and insulin-sensitivity when there is insulin-resistance, and in treating or preventing obesity, all in mammals that are in need of such treatments or that might benefit from such treatments, including human beings. The compounds are more generally useful in treating Type 2 diabetes (non-insulin dependent diabetes, or NIDDM). The compounds may also cause a beneficial reduction in triglycerides and lipids.

Compounds that inhibit PTP-1B may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with type 2 diabetes from needing insulin therapy.

Overexpression and elevated levels of PTP-1B have been observed in several cancer lines, including chronic myelogenous leukemia (CML), breast cancer, ovarian cancer, and prostate cancer, suggesting a regulatory role for PTP-1B in controlling kinase activity in these and other cancer cells. Thus inhibition of PTP-1B activity may constitute an important target for treating or preventing these and other cancers. The compounds may therefore be used to treat or prevent cancers, such as prostate cancer, breast cancer, ovarian cancer, multiple myeloma, leukemia, melanoma, lymphoma, renal cancer, and bladder cancer.

The compounds may also have utility in treating neurodegenerative diseases.

The compounds generally are efficacious in treating one or more of the following diseases: (1) type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) mixed or diabetic dyslipidemia, (8) hyperlipidemia, (9) hypertriglyceridemia, (10) hypercholesterolemia, (11) low HDL cholesterol, (12) high LDL cholesterol, (13) hyperapoBlipoproteinemia, (14) atherosclerosis and its sequelae, (14) vascular restenosis, (15) abdominal obesity, (16) retinopathy, (17) the metabolic syndrome, (18) high blood pressure, (19) insulin resistance, (19) cancer, and (20) neurodegenerative disease.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG—CoA reductase inhibitor such as lovastatin, simvastatin, rosuvastatin, pravastatin, fluvastatin, atorvastatin, rivastatin, or itavastatin. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions including hypercholesterolemia, atherosclerosis, hyperlipidemia, hypertriglyceridemia, dyslipidemia, high LDL, and low HDL.

The compounds of Formula I, or pharmaceutically accepatable salts thereof, may be used in methods for treating one or more of the diseases listed above by administering a therapeutically effective amount of the compound to a patient in need of treatment. The compounds of Formula I, or pharmaceutically acceptable salts thereof, may also be used in the manufacture of medicaments for treating one or more of the listed diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. In some cases, the daily dose may be as high as one gm. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 300 mg, 400 mg, 500 mg, and 750 mg. Other oral forms may also have the same or similar dosages. These tablets and capsules may be administered once a day, twice per day, three times per day, or four times per day. Administration once a day is generally preferred.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions as oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also optionally including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including hydroxylpropylmethylcellulose acetate (HPMCAS), hydroxylpropylmethyl cellulose (HPMCS), and polyvinylpyrrolidinones, including the homopolymer and copolymers.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant or mixture of surfactants such as hydroxypropylcellulose, polysorbate 80, and mono and diglycerides of medium and long chain fatty acids. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides such as metformin and phenformin;
(c) GPR40 agonists;
(d) dipeptidyl peptidase IV (DP-IV) inhibitors, such as sitagliptin, saxagliptin, and vildagliptin;
(e) insulin or insulin mimetics;
(f) sulfonylureas such as tolbutamide, glimepiride, glipizide, and related materials;
(g) α-glucosidase inhibitors (such as acarbose);
(h) agents which improve a patient's lipid profile, such as (i) HMG—CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as torcetrapib, and (viii) phenolic anti-oxidants, such as probucol;
(i) PPARα/γ dual agonists, such as muraglitazar, tesaglitazar, farglitazar, and JT-501;
(j) PPARδ agonists such as those disclosed in WO97/28149;
(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $β_3$ adrenergic receptor agonists;
(l) ileal bile acid transporter inhibitors;
(m) agents intended for use in inflammatory conditions such as aspirin, non-steroidal anti-inflammatory drugs, glucocorticoids, azulfidine, and cyclo-oxygenase 2 selective inhibitors;
(n) glucagon receptor antagonists;
(o) GLP-1,
(p) GIP-1,
(q) GLP-1 analogs, such as exendins, for example exenatide (Byetta), and
(r) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG—CoA reductase inhibitors, other PPAR agonists, GPR40 agonists, DP-IV inhibitors, and anti-obesity compounds.

Assays for Measuring Biological Activity

Activity in the compounds of this application is demonstrated using the following assays for PTP-1B-inhibiting activity.

Phosphatase Assay Protocol
Materials:
EDTA—ethylenediaminetetraacetic acid (Sigma)
DMH—N,N'-dimethyl-N,N'-bis(mercaptoacetyl)-hydrazine (synthesis published in *J. Org. Chem.* 56, pp. 2332-2337, (1991) by R. Singh and G. M. Whitesides and can be substituted with DTT—dithiothreitol Bistris-2,2-bis(hydroxymethyl)2,2',2"-nitrilotriethanol-(Sigma) Triton X-100—octylphenolpoly(ethylene-glycolether) 10 (Pierce)
Antibody: Anti-glutathione S-transferase rabbit (H and L) fraction (Molecular Probes)
Enzyme: Human recombinant PTP-1B, containing amino acids 1-320, fused to GST enzyme (glutathione S-transferase) or to FLAG peptide purified by affinity chromatography (Huyer et al, 1997, J. Biol. Chem., 272, 843-852). Wild type contains active site cysteine(215), whereas mutant contains active site serine(215).
Tritiated peptide: Bz-NEJJ-CONH$_2$, Mwt. 808, empirical formula, $C_{32}H_{32}T_2O_{12}P_2F_4$
Stock Solutions

| (10X) Assay Buffer | 500 mM Bistris (Sigma), pH 6.2, MW = 209.2 |
| | 20 mM EDTA (GIBCO/BRL) |
| | Store at 4° C. |

Prepare Fresh Daily:

| Assay Buffer (1X) | 50 mM Bistris |
| (room temp.) | 2 mM EDTA |
| | 5 mM DMH (MW = 208) |

Enzyme Dilution

| Buffer (keep on ice) | 50 mM Bistris |
| | 2 mM EDTA |
| | 5 mM DMH |
| | 20% Glycerol (Sigma) |
| | 0.01% Triton X-100 (Pierce) |

Antibody Dilution

| Buffer (keep on ice) | 50 mM Bistris |
| | 2 mM EDTA |

IC$_{50}$ Binding Assay Protocol:

Compounds (ligands) which potentially inhibit the binding of a radioactive ligand to the specific phosphatase are screened in a 96-well plate format as follows:

To each well is added the following solutions@25° C. in the following chronological order:
1. 110 μl of assay buffer.
2. 10 μl. of 50 nM tritiated BzN-EJJ-CONH$_2$ in assay buffer (1×)@25° C.
3. 10 μl. of testing compound in DMSO at 10 different concentrations in serial dilution (final DMSO, about 5% v/v) in duplicate@25° C.
4. 10 μl. of 3.75 μg/ml purified human recombinant GST-PTP-1B in enzyme dilution buffer.
5. The plate is shaken for 2 minutes.

6. 10 µl. of 0.3 µg/µl anti-glutathione S-transferase (anti-GST) rabbit IgG (Molecular Probes) diluted in antibody dilution buffer@25° C.

7. The plate is shaken for 2 minutes.

8. 50 µl. of protein A-PVT SPA beads (Amersham)@25° C.

9. The plate is shaken for 5 minutes. The binding signal is quantified on a Microbeta 96-well plate counter.

10. The non-specific signal is defined as the enzyme-ligand binding in the absence of anti-GST antibody.

11. 100% binding activity is defined as the enzyme-ligand binding in the presence of anti-GST antibody, but in the absence of the testing ligands with the non-specific binding subtracted.

12. Percentage of inhibition is calculated accordingly.

13. $IC_{50}$ value is approximated from the non-linear regression fit with the 4-parameter/multiple sites equation (described in: "Robust Statistics", New York, Wiley, by P. J. Huber (1981) and reported in nM units.

14. Test ligands (compounds) with larger than 90% inhibition at 10 µM are defined as actives.

Enzyme Assay PTP-1B

| | |
|---|---|
| Assay buffer | 50 mM Bis-Tris (pH = 6.3) |
| | 2 mM EDTA |
| | 5 mM N,N'-dimethyl-N,N'-bis(mercapto- |
| | acetyl)hydrazine (DMH) |
| Substrate | 10 mM fluorescein diphosphate (FDP) store at −20° C. |
| | (also can use 10 mM DiFMUP) |
| Enzyme | 50 mM Bis-Tris (pH = 6.3) |
| dilution | 2 mM EDTA |
| buffer | 5 mM DMH |
| | 20%(v/v) glycerol |
| | 0.01% Triton X-100 |

The assay was carried out at room temperature in 96 well plates. The reaction mixture in 170 µl contained 50 mM Bis-Tris (pH=6.3), 2 mM EDTA, 5 mM N,N'-dimethyl-N,N'bis(mercaptoacetyl)hydrazine (DMH) and 10 µM fluorescein diphosphare (FDP) or 6,8-difluoro-4-methylumbelliferyl phosphate (DiFMUP). 10 µl of 10 concentrations (serial dilution) of the test compound (inhibitor) dissolved in DMSO or DMSO alone for control was added to each well and the plate was mixed for 2 min. The reaction was initiated by adding 20 µl of diluted PTP-1B (50 nM for FDP, 0.5 nM for DiFMUP in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) or 6,8-difluoro-7-hydroxyl-4-coumarin (DiFMU) continuously for 15-30 min, using the Spectromax Gemini fluorescent plate reader (Molecular probes) with excitation of 440 nm and emission at 530 nm (cutoff filter at 525 nm) for FDP and excitation at 360 nm and emission at 450 nm (cutoff filter at 435 nm) for DiFMUP. All the assays were done at least in duplicate. The initial rate of FMP or DiFMU formation is plotted against the concentration of inhibitor and the data was fitted to 4-parameter equation and the inflection point of the fit is the $IC_{50}$.

Reversibility Assay

Same reagents as Enzyme Assay for PTP1B. IC50's were determined for compounds using 10 uM FDP and 5 nM PTP1B (final concentration) in 96-well plate as describe above. The phosphatase activity was followed for 10 minutes. A 40-fold dilution of the reaction mixture was obtained by transferring 5 ul of FDP reaction mixture into 195 ul assay buffer containing 10 uM DiFMUP another 96-well plate. The production of DiFMU was followed for 30 min. The data for both the FDP reaction and the DiFMUP reaction was fitted to a 4-parameter equation and the IC50's determined at the inflection point of the fit for both FDP and DiFMUP reactions. Compounds were reversible if IC50's shifted >20 fold from FDP to dilution into DiFMUP buffer.

Pharmacokinetics in Rats

Per Os Pharmacokinetics in Rats

Procedure:

The animals are housed, fed and cared for according to the Guidelines of the Canadian Council on Animal Care.

Male Sprague Dawley rats (325-375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

PEG 200/300/400: restricted to 2 mL/kg

Methocel 0.5%-1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram)

Intravenous Pharmacokinetics in Rats

Procedure:

The animals are housed, fed and cared for according to the Guidelines of the Canadian Council on Animal Care.

Male Sprague Dawley (325-375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1-2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

| | |
|---|---|
| Dextrose: | 1 mL/kg |
| 2-Hydroxypropyl-b-cyclodextrin | 1 mL/kg |
| DMSO (dimethylsulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram).

PTP-1B Intact Cell Assay

Construction of Recombinant Baculovirus Transfer Vectors and Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures* (Bulletin No. 1555). Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 µL of assay buffer, $2 \times 10^5$ PTP expressing cells or mock infected cells are dispensed into each well of 96-well polypropylene plates and pre-incubated either with a test compound or DMSO vehicle (3 µL), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16-18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50-100% of the baseline body weight. Oral glucose tolerance tests are done in the same manner as described above.

EXAMPLES

The following Examples are provided to illustrate the invention and are not to be construed as limiting the invention in any manner. The scope of the invention is defined by the appended claims.

Methods for preparing the compounds disclosed herein are illustrated in the following Schemes and Examples. Starting materials are either commercially available or made by known procedures in the literature or as illustrated. The present invention further provides processes for the preparation of compounds of formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention.

Example 1

3-((E)-2-{5-bromo-6-[difluoro(phosphono)methyl]-2-naphthyl}ethenyl)benzoic acid

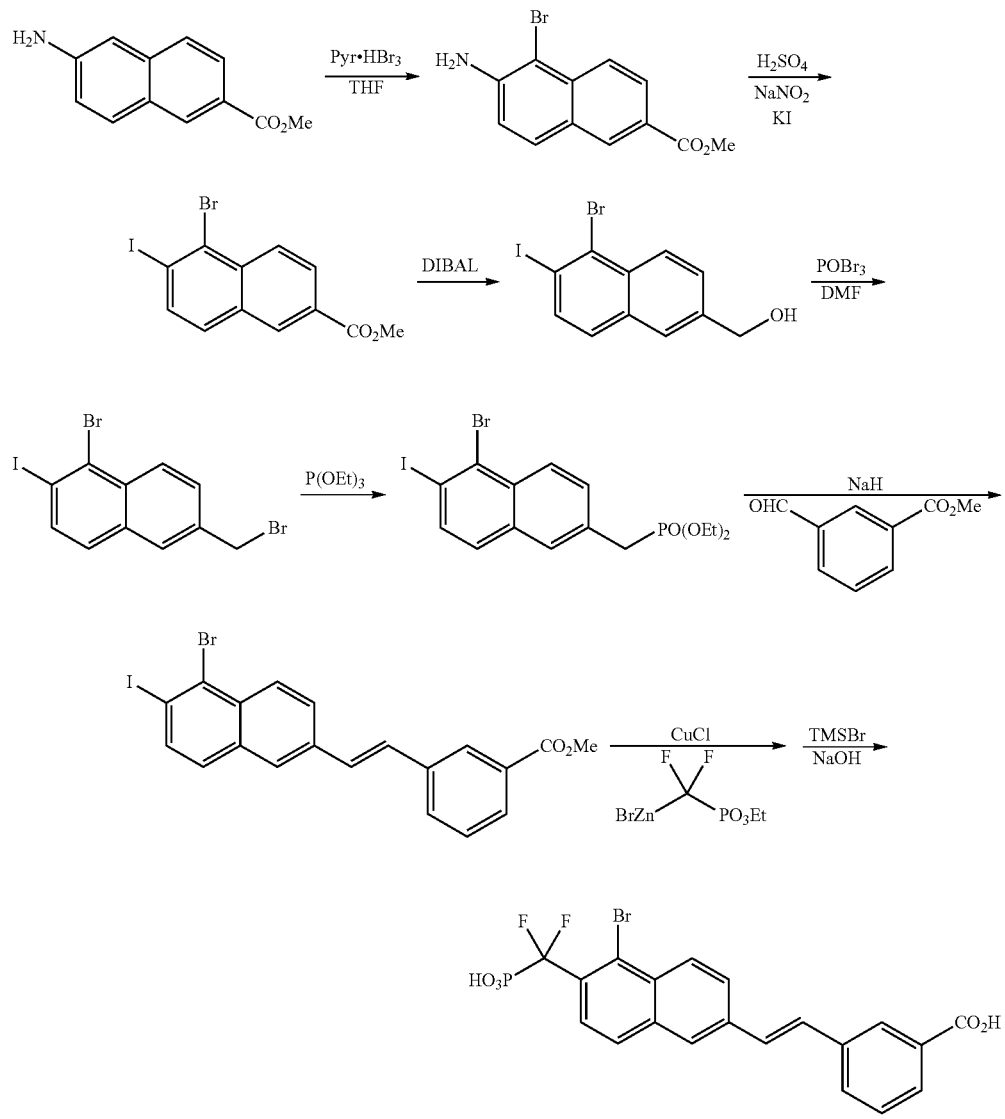

Step 1: Methyl 6-amino-5-bromo-2-naphthoate

To a solution of methyl 6-amino-2-naphthoate (0.5 g) in THF (10 ml) was added pyridinium tribromide (0.87 g). The reaction mixture was stirred at 0° C. for 1 h after which it was then filtered through a pad of $SiO_2$ and washed with hexane. The organic washings were evaporated to dryness and the residue was purified by flash chromatography eluting with hexane to afford the titled compound.

Step 2: Methyl 5-bromo-6-iodo-2-naphthoate

To a solution of methyl 6-amino-5-bromo-2-naphthoate (700 mg) in water (5 mL) at 0° C. was added $H_2SO_4$. The reaction mixture was stirred for 30 min. Then a solution of $NaNO_2$ (0.3 g) in 5 mL of water was added dropwise and the mixture was stirred for 90 min. To the solution at 0° C. was added a KI solution (1.1 g in 5 mL of water). The reaction was stirred overnight at rt. after which a saturated solution of $NH_4Cl$ was added to the mixture. The mixture was extracted with EtOAc and the extract dried over $Na_2SO_4$. The organic extracts were evaporated to dryness and the residue was purified by flash chromatography eluting with hexanes to afford the titled compound.

Step 3: (5-bromo-6-iodo-2-naphthyl)methanol

To a solution of methyl 5-bromo-6-iodo-2-naphthoate (0.37 g, 0.95 mmol) in toluene (10 mL) at −78° C. was added DIBAL (3 mL of a 1M solution in PhMe, 3 mmol) dropwise. The temperature was raised to 0° C. for 1 h. The reaction was quenched with 10 mL of 1M HCl, extracted with EtOAc and dried over $Na_2SO_4$. The organic extracts were evaporated to dryness to afford the titled compound.

Step 4: 1-bromo-6-(bromomethyl)-2-iodonaphthalene

To a solution of $POBr_3$ (662 mg, 2.3 mmol) in 4.5 mL of $CH_2Cl_2$ at 0° C. was added DMF (2.25 mL) dropwise. The reaction was stirred for 10 minutes and then a solution of (5-bromo-6-iodo-2-naphthyl)methanol (280 mg, 0.77 mmol) in 5 mL of $CH_2Cl_2$ was added. The reaction mixture was stirred for 30 minutes, quenched with a saturated solution of $NH_4Cl$, extracted with EtOAc and dried over $Na_2SO_4$. The organic extracts were evaporated to dryness to afford the titled product which was used as such in the next step.

Step 5: Diethyl (5-bromo-6-iodo-2-naphthyl)methylphosphonate

To 1-bromo-6-(bromomethyl)-2-iodonaphthalene (270 mg) from step 4 was added triethylphosphite (4 mL). The reaction mixture was heated at reflux for 1 hour followed by removal of excess triethylphosphite under high vacuum distillation yielding the titled product.

Step 6: Methyl 3-[(E)-2-(5-bromo-6-iodo-2-naphthyl)ethenyl]benzoate

To a solution of diethyl (5-bromo-6-iodo-2-naphthyl)methylphosphonate (250 mg) from step 5 in THF (5 mL) at 0° C. was added NaH (60% in mineral oil, 17 mg). The reaction mixture was stirred for 1 hour upon which methyl 3-formylbenzoate (85 mg) was added and stirring continued for 1 h at rt. The mixture was quenched with a saturated solution of $NH_4Cl$, extracted with EtOAc, dried over $Na_2SO_4$ and evaporated. The residue was purified by flash chromatography eluting with 5% EtOAc/hexanes to afford the titled product.

Step 7: Methyl 3-((E)-2-{5-bromo-6-[(diethoxyphosphoryl)(difluoro)methyl]-2-naphthyl}ethenyl)benzoate This product was obtained from methyl 3-[(E)-2-(5-bromo-6-iodo-2-naphthyl)ethenyl]benzoate by a reaction with ((diethoxyphosphinyl)difluoromethyl)zinc bromide following the procedure of S. Shibuya in *Tetrahedron* 1997, 53.3, 815.

Step 8: 3-((E)-2-{5-bromo-6-[difluoro(phosphono)methyl]-2-naphthyl}ethenyl)benzoic acid The hydrolysis of methyl 3-((E)-2-{5-bromo-6-[(diethoxyphosphoryl)(difluoro)methyl]-2-naphthyl}ethenyl)benzoate (35 mg) from step 7 was performed using TMSBr (2 mL) in 1 mL of $CH_2Cl_2$ at rt. overnight. The mixture was evaporated to dryness and the residue was dissolved in ethanol. It was evaporated to dryness again and the process was repeated 3 times. The reaction residue was dissolved in water and treated with NaOH 1N to afford the titled product as a sodium salt.

$^1$H NMR (500 MHz, $CD_3OD$): δ 8.52 (d, 1H), 8.30 (s, 1H), 8.15 (m, 2H), 7.95-8.05 (m, 3H), 7.72 (d 1H), 7.60 (m, 3H).

Example 2

3-((E)-2-{6-bromo-7-{difluoro(phosphono)methyl]-2-naphthyl}ethenyl)benzoic acid

Scheme 2

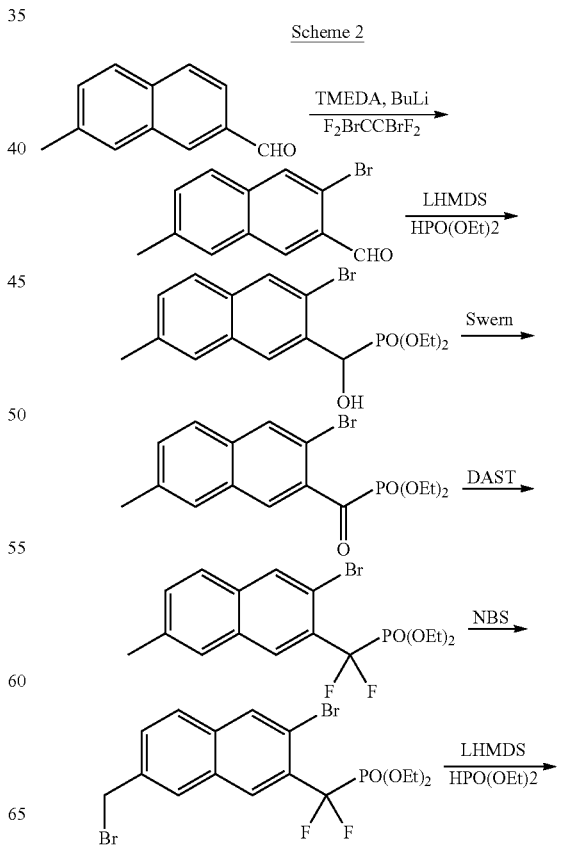

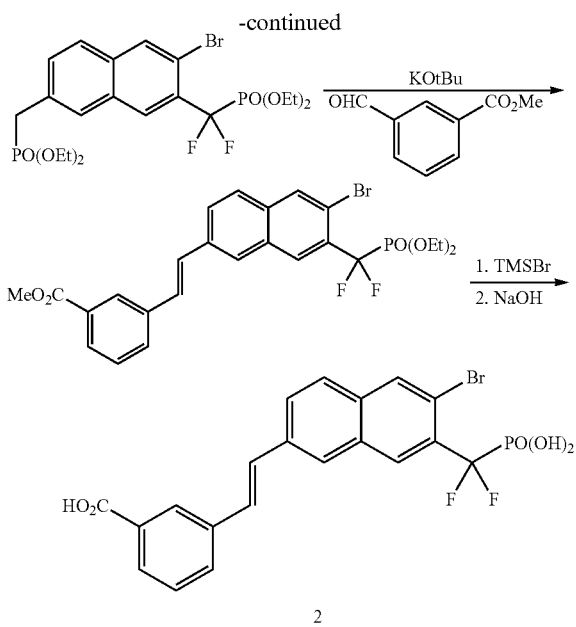

Step 1: 3-bromo-7-methyl-2-naphthadehyde

From 7-methyl-2-naphthaldehyde (430 mg), N,N,N'-trimethylethylenediamine (500 mg), BuLi (1.6M in hexanes, 4.95 mL) and tetrafluorodibromoethane (2.5 mL) the titled product was produced as described in the literature (Sun, Q., Lavoie E. J.; *Heterocycles;* 1996, 43, (4), 737-743).

Step 2: Diethyl (3-bromo-7-methyl-2-naphthyl)(hydroxy)methylphosphonate

To a solution of diethylphosphite (0.22 mL) in THF (5 mL) at −78° C. was added LiHMDS (1 equivalent of a 1M solution in THF). The reaction mixture was stirred for 1 h at −78° C. A solution of 3-bromo-7-methyl-2-naphthadehyde was added dropwise and the reaction was stirred overnight at 0° C. The reaction was quenched with a solution of saturated NH$_4$Cl, extracted with EtOAc and dried over Na$_2$SO$_4$. The organic extracts were evaporated to dryness and the residue was purified by flash chromatography eluting with 50-100% EtOAc/hexane to afford the titled product.

Step 3: Diethyl 3-bromo-7-methyl-2-naphthoylphosphonate

To a solution of oxalyl chloride (0.15 mL) in 2.5 mL of CH$_2$Cl$_2$ at −78° C. was added DMSO (0.23 mL). The reaction was stirred for 10 minutes after which a solution of diethyl (3-bromo-7-methyl-2-naphthyl)(hydroxy)methylphosphonate (160 mg), in 2.5 mL CH$_2$Cl$_2$ was added dropwise. The reaction was stirred for 1 h at −78° C. after which triethylamine (0.66 mL) was added to the mixture and the temperature was raised to rt. Water (5 mL) was added and the mixture was extracted with CH$_2$Cl$_2$. The organic extracts were combined, dried over Na$_2$SO$_4$ and evaporated to dryness to afford the titled product which was used as such in the next step.

Step 4: Diethyl (3-bromo-7-methyl-2-naphthyl)(difluoro)methylphosphonate

To a solution of diethyl 3-bromo-7-methyl-2-naphthoylphosphonate (160 mg), in CHCl$_3$ (3 mL) at −78° C. was added (diethylamino)sulfur trifluoride (0.44 mL). The reaction was stirred at rt. for 5 h and then was poured onto an ice/water/CH$_2$Cl$_2$ mixture. The organic extracts were backwashed with NH$_4$OH 50% in water and with brine. The extracts were then dried over Na$_2$SO$_4$ and evaporated to dryness. The residue was purified by flash chromatography eluting with 40% hexanes/EtOAc to afford the titled product.

Step 5: Diethyl[3-bromo-7-(bromomethyl)-2-naphthyl](difluoro)methylphosphonate

To a solution of diethyl (3-bromo-7-methyl-2-naphthyl)(difluoro)methylphosphonate (200 mg), in CCl$_4$ (12 mL) was added NBS (90 mg) and a catalytic amount of benzoyl peroxide. The mixture was refluxed for 2 hours and then diluted with hexanes. The solution was filtered through a pad of celite and washed with hexanes. The hexanes washings were evaporated to dryness to afford the titled product.

Step 6: Diethyl{6-bromo-7-[(diethoxyphosphoryl)(difluoro)methyl]-2-naphthyl}methylphosphonate To a solution of diethylphosphite (0.22 mL) in toluene (5 mL) at 0° C. was added NaH (60% in mineral oil, 20 mg). The reaction mixture was stirred for 1 hour and then a solution of diethyl[3-bromo-7-(bromomethyl)-2-naphthyl](difluoro)methylphosphonate (220 mg) in toluene (2 mL) was added dropwise. The reaction was stirred for 1 h at 0° C., quenched with a solution of saturated NH$_4$Cl, extracted with EtOAc and dried over Na$_2$SO$_4$. The organic extracts were evaporated to dryness and the residue was purified by flash chromatography eluting with 50% EtOAc/hexanes to afford the titled compound.

Step 7: Methyl 3-((E)-2-{6-bromo-7-[(diethoxyphosphoryl)(difluoro)methyl]-2-naphthyl}ethenyl)benzoate To a solution of diethyl{6-bromo-7-[(diethoxyphosphoryl)(difluoro)methyl]-2-naphthyl}methylphosphonate (190 mg), and methyl 3-formylbenzoate (60 mg) in degassed THF (5 mL) at −78° C. was added potassium tert-butoxide (0.35 mL of a 1M solution in THF) and the reaction mixture was stirred for 1 h at 0° C. The mixture was quenched with a saturated solution of NH$_4$Cl, extracted with EtOAc, dried over Na$_2$SO$_4$ and evaporated to dryness. The residue was purified by flash chromatography eluting with 25% EtOAc/hexanes to afford the titled product.

Step 8: 3-((E)-2-{6-bromo-7-{difluoro(phosphono)methyl]-2-naphthyl}ethenyl)benzoic acid The hydrolysis of methyl 3-((E)-2-{6-bromo-7-[(diethoxyphosphoryl)(difluoro)methyl]-2-naphthyl}ethenyl)benzoate (120 mg) from step 7, was done using TMSBr (2 mL) in 1 mL CH$_2$Cl$_2$ at rt overnight. The mixture was evaporated to dryness and the residue was dissolved in ethanol. It was evaporated to dryness again and the process was repeated 3 times. The reaction residue was dissolved in water and treated with NaOH 1N to afford the titled product as a sodium salt.

$^1$H NMR (500 MHz, CD$_3$OD): δ 8.84 (s, 1H), 8.22 (s, 1H), 8.12 (s, 1H), 8.05 (s, 1H), 7.88 (m, 2H), 7.78 (d, 1H), 7.70 (d, 1H), 7.40 (m, 3H),

Examples 3-6

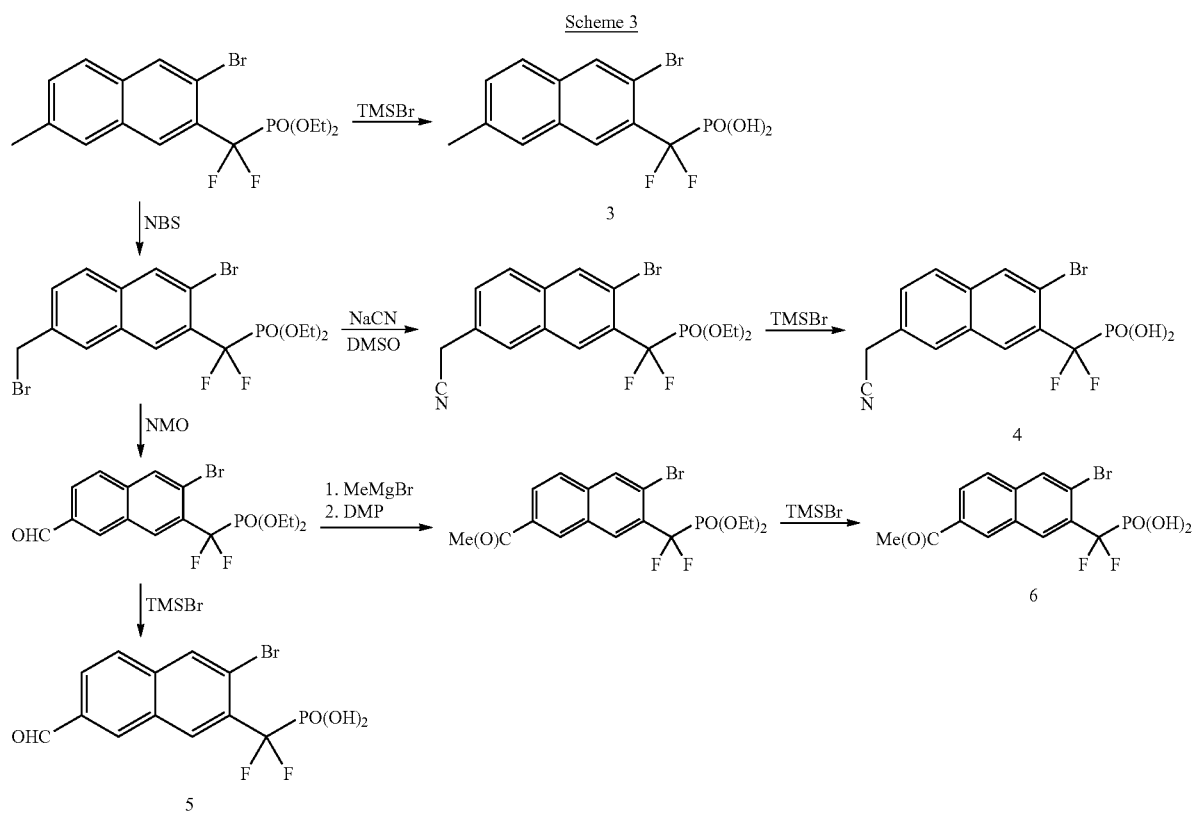

Scheme 3

Example 3

(3-bromo-7-methyl-2-naphthyl)(difluoro)methylphosphonic acid

Diethyl (3-bromo-7-methyl-2-naphthyl)(difluoro)methylphosphonate (0.1 g from step 4, example 2) was hydrolyzed with 2 mL of TMSBr in 1 mL of $CH_2Cl_2$ at rt. overnight. The mixture was evaporated to dryness and the residue was dissolved in ethanol. It was evaporated to dryness again and the process was repeated 3 times. The reaction residue was dissolved in water and treated with NaOH 1N to afford the titled product as a sodium salt.

$^1$H NMR (500 MHz, $CD_3OD$): δ 8.15 (d, 2H), 7.70 (m, 2H), 7.45 (d, 1H), 2.50 (s, 3H).

Example 4

[3-bromo-7-(cyanomethyl)-2-naphthyl](difluoro)methylphosphonic acid

To a solution of diethyl[3-bromo-7-(bromomethyl)-2-naphthyl](difluoro)methylphosphonate (0.06 g from step 5, example 2) in 3 mL of DMSO was added NaCN (18 mg). The reaction was stirred at rt. for 1 h. The reaction was quenched with water and extracted twice with ether. The organic extract were dried over $Na_2SO_4$ and evaporated. The residue was purified by flash chromatography eluting with 20% EtOAc/hexanes to afford the phophonate ester (20 mg): Diethyl[3-bromo-7-(cyanomethyl)-2-naphthyl](difluoro)methylphosphonate was hydrolyzed in 2 mL TMSBr at rt. overnight. The mixture was evaporated to dryness and the residue was dissolved in ethanol. It was evaporated to dryness again and the process was repeated 3 times. The reaction residue was dissolved in water and treated with NaOH 1N to afford the titled product as a sodium salt.

$^1$H NMR (500 MHz, $CD_3OD$): δ 8.40 (d, 1H), 8.34 (s, 1H), 8.13 (s, 1H), −8.05 (d, 1H), 7.72 (d 1H), 4.20 (s, 2H).

Example 5

(3-bromo-7-formyl-2-naphthyl)(difluoro)methylphosphonic acid

To a solution of diethyl[3-bromo-7-(bromomethyl)-2-naphthyl](difluoro)methylphosphonate (0.2 g from step 5, example 2) in 5 mL of dioxane was added N-methylmorpholine N-oxide (0.17 g). The reaction mixture was refluxed for 1 h. The mixture was quenched with a saturated solution of $NH_4Cl$ and the mixture was extracted with EtOAc and the extract dried over $Na_2SO_4$ and evaporated. The residue was purified by flash chromatography eluting with 10-20% EtOAc/hexanes to afford diethyl (3-bromo-7-formyl-2-naphthyl)(difluoro)methylphosphonate (0.15 grams) which was hydrolyzed with TMSBr (2 mL) in $CH_2Cl_2$ (1 mL) at rt. overnight. The mixture was evaporated to dryness and the residue was dissolved in ethanol. It was evaporated to dryness again and the process was repeated 3 times. The reaction residue was dissolved in water and treated with NaOH 1N to afford the titled product as a sodium salt.

1H NMR (500 MHz, CD3OD): δ 10.22 (s, 1H), 8.70 (s, 1H), 8.51 (s, 1H), 8.42 (s, 1H), 8.09 (m 2H).

Example 6

(7-acetyl-3-bromo-2-naphthyl)(difluoro)methylphosphonic acid

Step 1: Diethyl[3-bromo-7-(1-hydroxyethyl)-2-naphthyl](difluoro)methylphosphonate To a solution of diethyl(3-bromo-7-formyl-2-naphthyl)(difluoro)methylphosphonate (0.1 g from example 5) in THF (1 mL) at −78° C. was added MeMgBr (79 μL of a 3 N solution in THF). The temperature was raised to 0° C. and stirred for 1 h. The mixture was quenched with a saturated solution of NH₄Cl, extracted with EtOAc, the organic extracts dried over Na₂SO₄ and evaporated to dryness. The residue was purified by flash chromatography using 10-30% hexanes/EtOAc to afford the titled product.

Step 2: Diethyl(7-acetyl-3-bromo-2-naphthyl)(difluoro)methylphosphonate

To a solution of diethyl[3-bromo-7-(1-hydroxyethyl)-2-naphthyl](difluoro)methylphosphonate (20 mg) from step 1, in CH₂Cl₂ (2 mL) at 0° C. was added Dess-Martin reagent (24 mg). The temperature was raised to rt and the reaction stirred for 1 h. The reaction was filtered on a pad of SiO₂ eluting with 30% EtOAc/hexanes and the organics were evaporated to dryness. The residue was dissolved and hydrolysed with neat TMSBr (3 mL) and stirred at rt. overnight. The mixture was evaporated to dryness and the residue was dissolved in ethanol. It was evaporated to dryness again and the process was repeated 3 times. The reaction residue was dissolved in water, co-distilled with toluene and pumped with high vacuum to afford the titled product. ¹H NMR (500 MHz, CD₃OD): δ 8.79 (d, 1H), 8.50 (s, 1 H), 8.39 (s, 1H), 8.15 (d, 1H), 8.02 (d 1H), 2.75 (s, 3H).

Example 7

[(3-bromo-6-cyano-2-naphthyl)(difluoro)methyl]phosphonic acid

Scheme 4

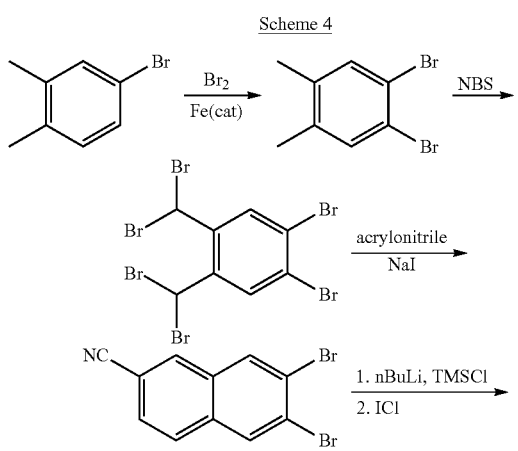

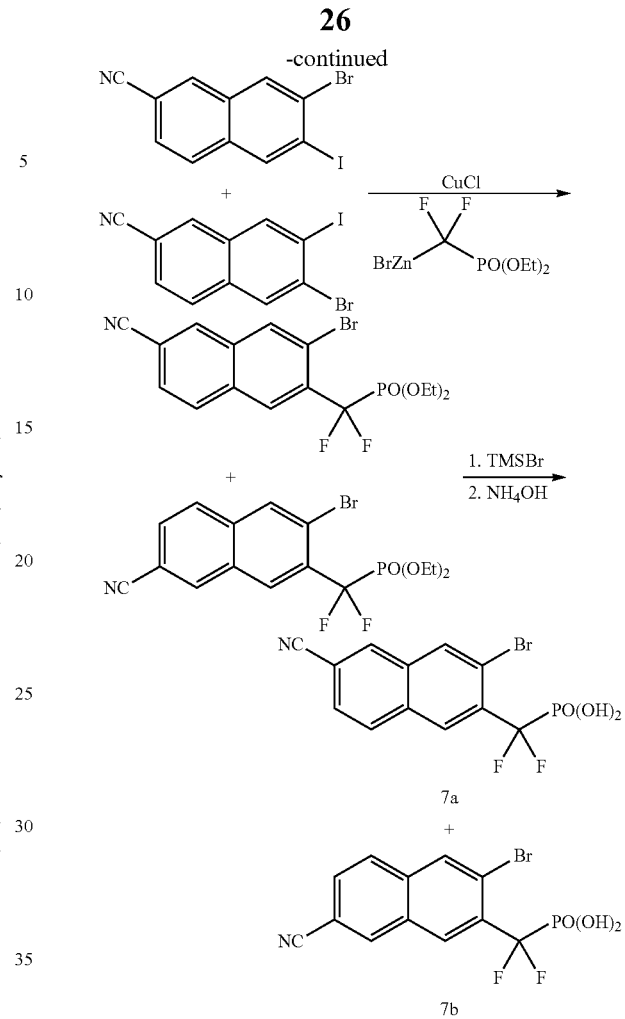

Steps 1-3: 6,7-dibromo-2-naphthonitrile

According to the literature procedure (Hanack, M., Grobhans, R.; *Chem. Ber.* 1992, 125, 1243-1247), 6,7-dibromo-2-naphthonitrile, can be prepared in 2 steps from commercially available, 4,5-dibromo-o-xylene or in 3 steps from commercially available, 4-bromo-o-xylene.

Step 4: 7-bromo-6-iodo-2-naphthonitrile and 6-bromo-7-iodo-2-naphthonitrile

To a solution of 6,7-dibromo-2-naphthonitrile (15 g) and TMSCl (6.73 mL) in THF (250 mL) at −78° C. was added n-BuLi (53 mL, 1.6 M in hexanes, precooled to −20° C.) rapidly with vigorous stirring and the mixture was stirred for an additional 5 min and quenched with saturated NH₄Cl. The mixture was then extracted with ethyl acetate and the organic layer was washed with water and brine, dried over MgSO₄ and filtered. The filtrate was concentrated and the crude was purified by column chromatograph to give the desired product as a yellow solid.
¹H NMR (400 MHz, acetone-d₆) (a mixture of two regioisomers): δ 8.53 (s, 1H), 8.42 (s, 1H), 8.33 (s, 1H), 8.30 (S, 1h), 8.23 (S, 1h), 8.20 (S, 1h), 8.18 (d, 1H), 8.07 (d, 1H), 7.82-7.77 (m, 2H), 0.50 (s, 18H).
To a solution of the above product in dichloromethane (250 mL) was added excess ICl and the mixture was stirred at rt. for 1 h. The solution was then washed with 10% Na₂S₂O₃ until all ICl was consumed. The solution was then washed with water, brine, dried over MgSO₄ and filtered. The filtrate was concentrated and the residue was recrystallized from ether/hexanes to give the desired product.

¹H NMR (400 MHz, acetone-$d_6$) (a mixture of two regioisomers): δ 8.74 (s, 1H), 8.73 (s, 1H), 8.46-8.44 (m, 4H), 8.10-8.07 (m, 2 h), 7.84-7.81 (m, 2H).

Step 5: diethyl[(3-bromo-6-cyano-2-naphthyl)(difluoro)methyl]phosphonate and diethyl[(3-bromo-7-cyano-2-naphthyl)(difluoro)methyl]phosphonate A flame dried round bottomed flask was charged with CuBr (99.999%) and THF (10 mL), followed by ((diethoxyphosphinyl)difluoromethyl)zinc bromide (29 mL, 1.72 M in THF) following the procedure of S. Shibuya in *Tetrahedron* 1997, 53.3, 815.). The suspension was stirred under $N_2$ for 15 minutes. 7-Bromo-6-iodo-2-naphthonitrile (7.1 g) was then added as a solid and the mixture was heated to 45° C. overnight and cooled to rt. The suspension was then quenched with half saturated NH₄Cl and extracted with 1:1 ether/ethyl acetate (3×). The extracts were processed as usual to give the crude product which was first purified by flash chromatograph (40% ethyl acetate in hexanes). The two regioisomers were then separated by HPLC. Eluting with 50% ethyl acetate/hexanes first gave the less polar isomer diethyl[(3-bromo-7-cyano-2-naphthyl)(difluoro)methyl]phosphonate.

¹H NMR (400 MHz, acetone-$d_6$): δ 8.72 (s, 1H), 8.54 (s, 1H), 8.46 (s, 1H), 8.19 (d, 1H), 7.95 (d, 1H), 4.26 (m, 4H), 1.33 (t, 6H).

Continued elution gave the more polar isomer, diethyl[(3-bromo-6-cyano-2-naphthyl)(difluoro)methyl]-phosphonate.

¹H NMR (400 MHz, acetone-$d_6$): δ 8.56 (s, 2H), 8.43 (s, 1H), 8.35 (d, 1H), 7.93 (d, 1H), 4.26 (m, 4H), 1.33 (t, 6H).

Step 6: [(3-bromo-7-cyano-2-naphthyl)(difluoro)methyl]phosphonic acid (7a)

A solution of diethyl[(3-bromo-7-cyano-2-naphthyl)(difluoro)methyl]phosphonate (2.2 g) in dichloromethane (5 mL) and TMSBr (7 mL) was stirred overnight and concentrated. The residue was co-evaporated with dichloromethane (2×), ethanol/water (2×) and then dissolved in 20 mL of methanol. Ammonia (30%) was then added with vigorous stirring and the mixture was concentrated and co-evaporated with methanol (3×). The solid residue was washed with ether to give the desired product as a white powder. MS (–ESI): m/z 360.0 and 361.9 (M–1)⁻.

Note: [(3-bromo-6-cyano-2-naphthyl)(difluoro)methyl] phosphonic acid (7b) was obtained in a similar manner as described in step 6. MS (–ESI): m/z 360.0, 361.9.

Example 8a

[{2-[(phenylamino) carbonyl]-6-bromoquinolin-7-yl}(difluoro)methyl]phosphonic acid Scheme 5

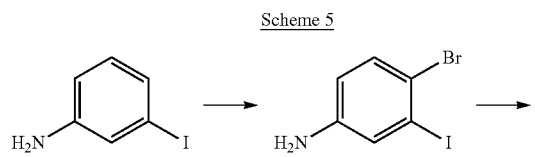

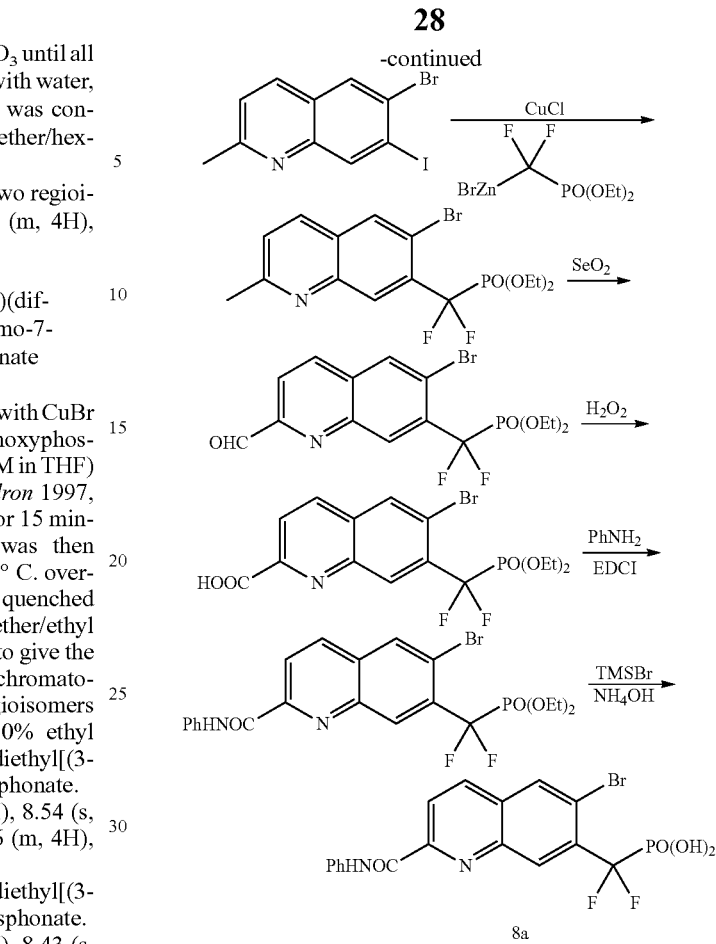

8a

Step 1: (4-bromo-3-iodophenyl)amine

To a solution of 3-iodoaniline (12 mL, 100 mmol) in 400 mL CH₂Cl₂ at –10° C. was added in portions 2,4,4,6-tetrabromo-2,5-cyclohexadienone (45.1 g, 110 mmol) while maintaining an internal temperature of –10° C. After stirring for 4 hours, 150 mL of 1N NaOH was added, and the product was extracted with CH₂Cl₂. The combined extracts were washed with water and then brine and dried over Na₂SO₄. After concentration in vacuo the crude product was recrystallized with 2:1 hexanes:toluene to yield the desired product.

Step 2: 6-bromo-7-iodo-2-methylquinoline

To (4-bromo-3-iodophenyl)amine (11.93 g, 40 mmol) was added conc HCl (6 ml), p-chloranil (9.83 g, 1 equiv.) and isopropanol (20 ml) and the mixture was heated to reflux. A solution of crotonaldehyde (3.98 ml) in isopropanol (3.8 ml) was then added at a rate of 0.1 ml/min using a syringe pump and the mixture was stirred at reflux for another 40 min after the end of the addition. The mixture was cooled to r.t., diluted with EtOAc and 5% aq. NH₄OH. The products were extracted in EtOAc and the organic layer was washed several times with water, brine, and dried over Na₂SO₄. The crude material was dissolved as much as possible in 300 ml boiling toluene and purified by flash chromatography on silica with a gradient of EtOAc/toluene 0 to 5%. The first product was 6-bromo-7-iodo-2-methylquinoline followed by its isomer 6-bromo-5-iodo-2-methylquinoline.

6-bromo-7-iodo-2-methylquinoline: ¹H NMR (400 MHz, acetone-$d_6$): δ 8.58 (s, 1H), 8.32 (s, 1H), 8.20 (d, 1H), 7.48 (d, 1H), 2.68 (s, 3H).

6-bromo-5-iodo-2-methylquinoline: $^1$H NMR (400 MHz, acetone-$d_6$): δ 8.45 (d, 1H), 8.01 (d, 1H), 7.92 (d, 1H), 7.53 (d, 1H), 2.72 (s, 3H).

Step 3: diethyl[(6-bromo-2-methylquinolin-7-yl)(difluoro)methyl]phosphonate

This product was obtained from 6-bromo-7-iodo-2-methylquinoline by a reaction with ((diethoxyphosphinyl)difluoromethyl)zinc bromide following the procedure of S. Shibuya in *Tetrahedron* 1997, 53.3, 815.

Step 4: diethyl[(6-bromo-2-formylquinolin-7-yl)(difluoro)methyl]phosphonate

To the product of step 3 (1.24 g, 3.04 mmol) in 15 ml dioxane was added selenium dioxide (388 mg, 1.15 equiv. dried under vacuum with a torch) and the mixture was heated to 100° C. for 1.3 h. The solvent was evaporated and the residue purified by flash chromatography on silica with 30% EtOAc/toluene to yield the title product as a yellow solid.
$^1$H NMR (500 MHz, acetone-$d_6$) δ 10.16 (s, 1H), 8.63, (d, 1H), 8.48 (s, 1H), 8.53 (s, 1H), 8.13 (d, 1H), 4.30 (m, 4H), 1.33 (t, 6H).

Step 5: 6-bromo-7-[(diethoxyphosphoryl)(difluoro)methyl]quinoline-2-carboxylic acid As described in the literature (Synthesis, 1993, 295), to the product of step 4 (105 mg, 0.25 mmol) in 1 ml formic acid was added 30% hydrogen peroxide (0.13 mL, 1 mmol) dropwise and the mixture was stirred overnight at rt. The solvent was evaporated and absolute ethanol was added. This was repeated 3 times and after evaporation of the remaining ethanol yielded the title product as an oil.
$^1$H NMR (500 MHz, acetone-$d_6$) δ 8.63, (s, 1H), 8.49 (s, 2H), 8.45 (s, 1H), 4.30 (m, 4H), 1.33 (t, 6H).

Step 6: diethyl[{2-[(phenylamino)carbonyl]-6-bromoquinolin-7-yl}(difluoro)methyl]phosphonate To the product of step 5 (109 mg) in 5 mL CH$_2$Cl$_2$ was added EDCl (96 mg), aniline (0.1 mL) and Hunig's base (0.1 mL). The solution was stirred at ambient temperature for 3 hours and after concentration and flash chromatography on silica with a gradient of 10-25% EtOAc/toluene the amide was obtained.
NMR (500 MHz, CDCl$_3$) δ 10.2, (s, 1H), 8.6 (s, 1H), 8.5 (d, 1H), 8.45 (d, 1H), 8.4 (s, 1H), 7.4-7.0 (m, 5H), 4.30 (m, 4H), 1.33 (t, 6H).

Step 7: [{2-[(phenylamino)carbonyl]-6-bromoquinolin-7-yl}(difluoro)methyl]phosphonic acid (8)

A solution of diethyl[(3-bromo-7-cyano-2-naphthyl)(difluoro)methyl]phosphonate (2.2 g) in dichloromethane (5 mL) and TMSBr (7 mL) was stirred overnight and concentrated. The residue was co-evaporated with dichloromethane (2×), ethanol/water (2×) and then dissolved in 20 mL of methanol. Ammonia (30%) was then added with vigorous stirring and the mixture was concentrated and co-evaporated with methanol (3×). The solid residue was washed with ether to give the desired product as a white powder. MS (−ESI): m/z 457.2 and 456.3 (M−1)$^-$.

The table below shows derivatives similar to Example 8a that were prepared using a method analogous to the above scheme:

TABLE 1

| Example | R | MS (neg) |
|---|---|---|
| 8a | Ph | 457, 456 |
| 8b | H | 381, 379 |
| 8c | Me | 395, 393 |
| 8d | Bn | 471, 469 |
| 8e | 3-F—Ph | 475, 473 |

Examples 9a-9i (6-bromo-2-substitutedquinolin-7-yl)(difluoro)methyl]phosphonic acids The compounds in the following table were prepared as shown in the footnotes from intermediates described in Scheme 5 (example 8) and Scheme 6 (for Example 9-I, which is the last entry in Table 2).

Example 9i (Table 2): Diammonium [(6-bromo-2-cyanoguinolin-7-yl)(difluoro)methyl]phosphate

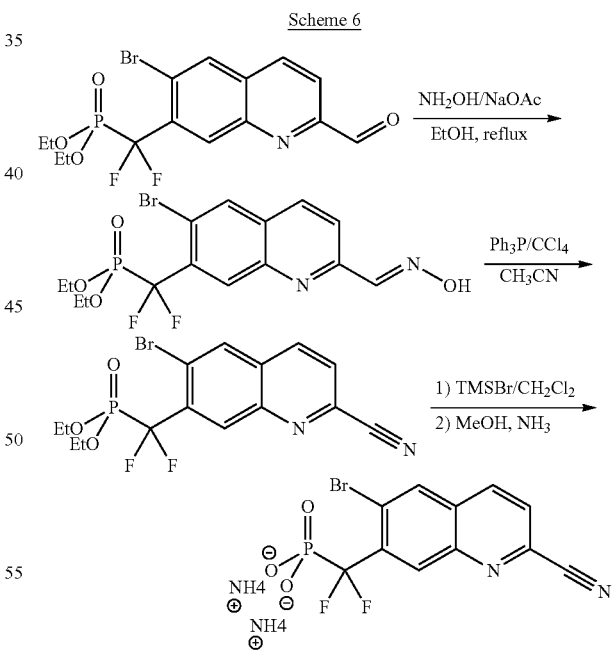

Scheme 6

Step 1 diethyl[(6-bromo-2-((hydroxyimino)methyl)quinolin-7-yl)(difluoro)methyl]phosphonate To a stirred solution of diethyl[(6-bromo-2-formylquinolin-7-yl)(difluoro)methyl]phosphonate (525 mg, 1.244 mmol) [Example 8, Step 4] in ethanol (12 mL) at room temperature were added hydroxylamine hydrochloride (130 mg, 1.865 mmol) and sodium acetate (508 mg, 3.73 mmol). The reaction mixture was stirred at 70° C. for 1 hour. It was then poured into aqueous sodium hydrogen carbonate and extracted with ethyl acetate (100 mL), washed with aqueous sodium hydrogen carbonate (2×), brine, dried with $MgSO_4$, and concentrated in vacuo to give crude diethyl[(6-bromo-2-[(E)-(hydroxyimino)methyl]quinolin-7-yl)(difluoro)methyl]phosphonate.

$^1$H NMR δ (ppm)(acetone-$d_6$): 11.19 (1H, s), 8.44 (1H, s), 8.39 (1H, d, J=8.72 Hz), 8.36 (1H, s), 8.29 (1H, s), 8.13 (1H, d, J=8.72 Hz), 4.34-4.26 (4H, m), 0.36-1.29 (6 H, m).

Step 2 diethyl[(6-bromo-2-cyanoquinolin-7-yl)(difluoro)methyl]phosphonate

To a stirred solution of diethyl[(6-bromo-2-[(E)-(hydroxyimino)methyl]quinolin-7-yl)(difluoro)methyl]phosphonate (520 mg, 1.189 mmol) in acetonitrile (30 mL) at room temperature were added triphenylphosphine (1.248 g, 4.76 mmol) and carbon tetrachloride (230 μL, 2.383 mmol). The reaction mixture was stirred at 100° C. for 1 hour. It was concentrated to dryness in vacuo, pre-adsorbed in silica gel for flash chromatography eluting with ethyl acetate in toluene (20% to 30%) to afford diethyl[(6-bromo-2-cyanoquinolin-7-yl)(difluoro)methyl]phosphonate.

$^1$H NMR δ (ppm)(acetone-$d_6$): 8.72 (1H, d, J=8.52 Hz), 8.63 (1H, s), 8.43 (1 H, s), 8.13 (1H, d, J=8.52 Hz), 4.36-4.26 (4H, m), 1.41-1.29 (6H, m). MS (+ESI)=419.0 and 421.0.

Step 3 diammonium[(6-bromo-2-cyanoquinolin-7-yl)(difluoro)methyl]phosphate

To a stirred solution of diethyl[(6-bromo-2-cyanoquinolin-7-yl)(difluoro)methyl]phosphonate (370 mg, 0.883 mmol) in dichloromethane (9) at 0° C. was added dropwise bromotrimethylsilane (1.15 mL, 8.83 mmol). The reaction mixture was stirred at room temperature overnight. It was concentrated to dryness, and co-evaporated with dichloromethane (2×). Ethanol (5 mL) was added to the residue, which was stirred for 20 minutes. It was concentrated to dryness and co-evaporated with ethanol (2×). The residue was dissolved in methanol (8 mL) and 2.0 M ammonia in methanol (4.4 mL, 8.80 mmol) was added dropwise. It was stirred for 20 minutes, concentrated to dryness and suspended in diethyl ether. The precipitate was filtered to afford diammonium[(6-bromo-2-cyanoquinolin-7-yl)(difluoro)methyl]phosphonate.

$^1$H NMR δ (ppm)($CD_3OD$): 8.69 (1H, s), 8.48 (1H, d, J=8.50 Hz), 8.39 (1H, s), 7.89 (1H, d, J=8.50 Hz), MS (−ESI)=361.0 and 363.0.

TABLE 2

| Example | Structure | MS (neg) |
|---|---|---|
| 9a | (structure) | 350, 352 |
| 9b | (structure) | 350, 352 |
| 9c | (structure) | 364, 366 |
| 9d | (structure) | 380, 382 |
| 9e | (structure) | 378, 380 |
| 9f | (structure) | 398, 400 |
| 9g | (structure) | 379, 381 |
| 9h | (structure) | 407, 409 |
| 9i | (structure) | 361, 363 |

9a) Prepared from the TMSBr hydrolysis of diethyl[(6-bromo-2-methylquinolin-7-yl)(difluoro)methyl]phosphonate (Example 8, step 3) as in Example 1, step 8.

9b) Prepared from 6-bromo-5-iodo-2-methylquinoline (Example 8, step 2) by a reaction with ((diethoxyphosphinyl)difluoromethyl)zinc bromide (S. Shibuya in *Tetrahedron* 1997, vol 53, no 3, 815) followed by a TMSBr hydrolysis as in Example 1, step 8

9c) Prepared from the TMSBr hydrolysis of diethyl[(6-bromo-2-formylquinolin-7-yl)(difluoro)methyl]phosphonate (Example 8, step 4) as in Example 1, step 8.

9d) Prepared by the methylmagnesium addition to diethyl[(6-bromo-2-formylquinolin-7-yl)(difluoro)methyl]phosphonate (Example 8, step 4) at −78 to −10° C. in THF, followed by a TMSBr hydrolysis as in Example 1, step 8.

9e) Prepared by oxidation of diethyl[(6-bromo-2-(1-hydroxyethyl)quinolin-7-yl)(difluoro)methyl]phosphonate (Example 9d) with $MnO_2$ in EtOAc at r.t. for 1.5 h, followed by a TMSBr hydrolysis as in Example 1, step 8.

9f) Prepared by reaction of diethyl[(6-bromo-2-(1-hydroxyethyl)quinolin-7-yl)(difluoro)methyl]phosphonate (Example 9d) with methanesulfonyl chloride and a large excess of DBU in $CH_2Cl_2$ at r.t. for several hours, followed by a TMSBr hydrolysis as in Example 1, step 8.

9g) Prepared by reaction of diethyl[(6-bromo-2-formylquinolin-7-yl)(difluoro)methyl]phosphonate (example 8, step 4) with hydroxylamine hydrochloride (2 equiv) and sodium acetate trihydrate (4 equiv) in refluxing ethanol for 5 h, followed by a TMSBr hydrolysis as in Example 1, step 8.

9h) Prepared by reacting diethyl[(6-bromo-2-acetylquinolin-7-yl)(difluoro)methyl]phosphonate (Example 9e) with methoxyamine hydrochloride (3 equiv) in pyridine at 80° C. for 2 h, followed by a TMSBr hydrolysis as in Example 1, step 8.

9i) Prepared by dehydration of diethyl[(6-bromo-2-((hydroxyimino)methyl)quinolin-7-yl)(difluoro)methyl]phosphonate (Example 9g) with triphenylphosphine and $CCl_4$ in $CH_3CN$ (*Synth. Commun.* 1990, 2785), followed by a TMSBr hydrolysis (Example 9i).

What is claimed is:

1. A compound of structural formula Ia:

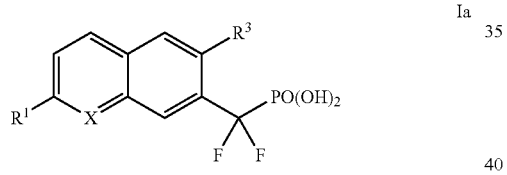

or a pharmaceutically acceptable salt thereof;
wherein X is CH;
$R^1$ is selected from the group consisting of (a) $C_{1-3}$ alkyl optionally substituted with 1-3 halogens and optionally with one group selected from —OH, —$OC_{1-3}$alkyl optionally substituted with 1-3 halogens, —$SO_xC_{1-3}$alkyl, and —CN, (b) —C(=O)H, (c) —C(=O)$C_{1-3}$alkyl optionally substituted with 1-3 halogens, (d) —HC=NOH, (e) —($CH_3$)C=NOH, (f) —HC=$NOC_{1-3}$alkyl optionally substituted with 1-3 halogens, (g) —($CH_3$)C=$NOC_{1-3}$alkyl optionally substituted with 1-3 halogens, (h) —C(=O)$OC_{1-3}$alkyl optionally substituted with 1-3 halogens, (i) —C(=O)$NHR^6$, (j) —CH=CH-Phenyl wherein —CH=CH— is optionally substituted with 1-2 substituents independently selected from halogen and $C_{1-2}$alkyl optionally substituted with 1-3 F, (k) —$CH_2CH_2$-Phenyl wherein —$CH_2CH_2$— is optionally substituted with 1-4 substituents independently selected from halogen and $C_{1-2}$ alkyl optionally substituted with 1-3 F, (l) Phenyl, (m) -HET-Phenyl, wherein HET is a 5- or 6-membered heteroaromatic ring containing 1-3 heteroatoms selected from O, N and S, (n) —C≡C-Phenyl, and (o) —$CH_2$-Phenyl, wherein the —$CH_2$- group of —$CH_2$-Phenyl is optionally substituted with 1-2 substituents independently selected from halogen and $C_{1-2}$ alkyl optionally substituted with 1-3 F, wherein Phenyl and HET in all occurrences are optionally substituted with 1-3 substituents independently selected from (i) halogen, (ii) —C(=O)$OC_{1-3}$alkyl optionally substituted with 1-3 halogens, (iii) —C(=O)OH, (iv) $C_{1-3}$alkyl optionally substituted with 1-3 halogens, (v) —$OC_{1-3}$ alkyl optionally substituted with 1-3 halogens, (vi) —$SO_x$Me, and (vii) —$SO_2NH_2$;

$R^3$ is halogen;

$R^6$ is selected from the group consisting of H, $C_{1-3}$alkyl optionally substituted with 1-3 halogens, Phenyl, and —$CH_2$-Phenyl, wherein Phenyl in both occurrences is optionally substituted with 1-3 substituents independently selected from (i) halogen, (ii) —C(=O)$OC_{1-3}$ alkyl optionally substituted with 1-3 halogens, (iii) —C(=O)OH, (iv) $C_{1-3}$alkyl optionally substituted with 1-3 halogens, and (v) —$OC_{1-3}$alkyl optionally substituted with 1-3 halogens; and x is 0, 1, or 2.

2. The compound of claim 1 selected from the group consisting of:

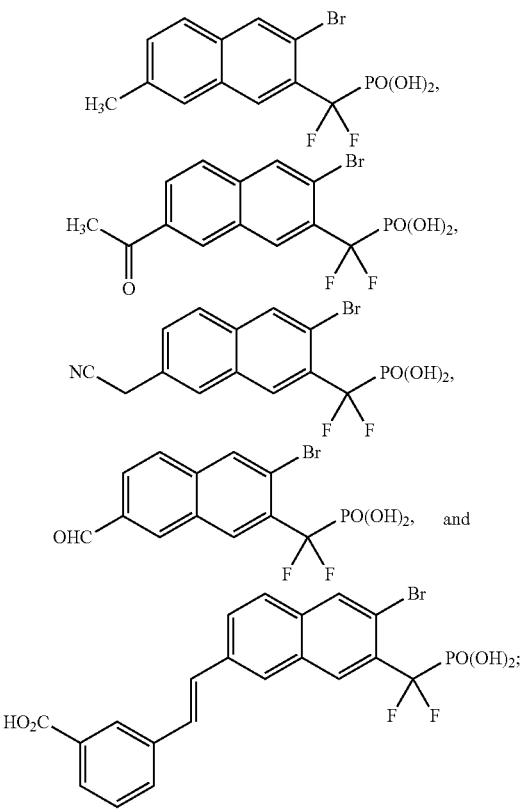

or a pharmaceutically acceptable salt thereof.

3. The compound of claim 2 which is:

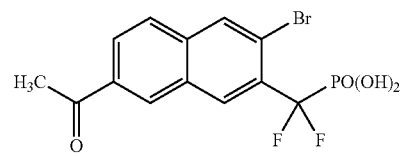

or a pharmaceutically acceptable salt thereof.

4. The compound of claim 2 which is:

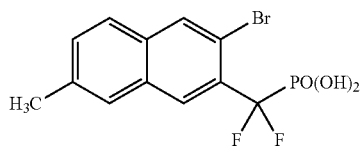

or a pharmaceutically acceptable salt thereof.

5. The compound of claim 2 which is:

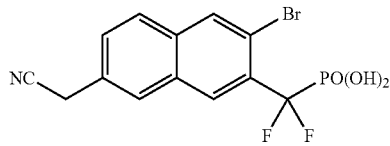

or a pharmaceutically acceptable salt thereof.

6. A pharmaceutical composition comprising a compound of claim 1, or a pharmaceutically acceptable salt thereof, and a pharmaceutically acceptable carrier.

7. A method of treating type 2 diabetes mellitus in a patient in need of treatment comprising the administration to the patient of a therapeutically effective amount of the compound of claim 1, or a pharmaceutically acceptable salt thereof.

8. A pharmaceutical composition comprising
(1) a compound of claim 1 or a pharmaceutically acceptable salt thereof;
(2) one or more compounds selected from the group consisting of:
(a) PPAR gamma agonists and partial agonists;
(b) biguanides;
(c) GPR40 agonists;
(d) dipeptidyl peptidase IV (DP-IV) inhibitors;
(e) insulin or an insulin mimetic;
(f) sulfonylureas;
(g) α-glucosidase inhibitors;
(h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (h) acyl CoA:cholesterol acyltransferase (ACAT) inhibitors, (i) CETP inhibitors, and (j) phenolic anti-oxidants;
(i) PPARα/γ dual agonists,
(j) PPARδ agonists,
(k) antiobesity compounds,
(l) ileal bile acid transporter inhibitors;
(m) anti-inflammatory agents;
(n) glucagon receptor antagonists;
(o) GLP-1;
(p) GIP-1;
(q) GLP-1 analogs; and
(r) HSD-1 inhibitors; and
(3) a pharmaceutically acceptable carrier.

\* \* \* \* \*